(12) United States Patent
Carr

(10) Patent No.: US 8,002,751 B2
(45) Date of Patent: Aug. 23, 2011

(54) FILTER NEEDLE

(76) Inventor: Sue Carr, Dickerson, MD (US)

( * ) Notice: Subject to any disclaimer, the term of this patent is extended or adjusted under 35 U.S.C. 154(b) by 153 days.

(21) Appl. No.: 11/975,079

(22) Filed: Oct. 17, 2007

(65) Prior Publication Data

US 2008/0097353 A1 Apr. 24, 2008

Related U.S. Application Data

(60) Provisional application No. 60/853,444, filed on Oct. 23, 2006.

(51) Int. Cl.
*A61M 5/00* (2006.01)

(52) U.S. Cl. ........ 604/190; 604/181; 604/187; 604/192; 604/263

(58) Field of Classification Search .................. 604/181, 604/187, 190, 272, 110, 192, 263, 905
See application file for complete search history.

(56) References Cited

U.S. PATENT DOCUMENTS

| | | | |
|---|---|---|---|
| 2,626,603 A | 1/1953 | Gabriel | |
| 2,689,564 A | 9/1954 | Adams et al. | |
| 2,775,240 A | 12/1956 | Morrisey et al. | |
| 2,827,081 A | 3/1958 | Little | |
| 2,833,281 A | 5/1958 | Krug | |
| 2,857,913 A | 10/1958 | Miskel | |
| 2,864,366 A | 12/1958 | Miskel | |
| 2,972,991 A | 2/1961 | Burke | |
| 3,008,570 A | 11/1961 | Roehr et al. | |
| 3,757,780 A * | 9/1973 | Ishikawa | 604/190 |
| 4,137,917 A | 2/1979 | Cohen | |
| 4,180,071 A | 12/1979 | Oiwa | |
| 4,316,462 A | 2/1982 | Baker | |
| 5,158,550 A * | 10/1992 | Scholl, Jr. | 604/110 |
| 6,629,962 B2 * | 10/2003 | Correa et al. | 604/272 |
| 6,958,055 B2 * | 10/2005 | Donnan et al. | 604/192 |

* cited by examiner

*Primary Examiner* — Theodore Stigell
*Assistant Examiner* — Laura Schell

(57) ABSTRACT

A single in-line filter hollow needle has an outer wall, a proximal end, a distal end with a pointed tip and a central opening between the ends for communicating fluids therethrough. The proximal end is secured to a luer lock for removable connection to a syringe. A filter is located in the central opening proximate to the tip. The outer wall of the needle has a frangible deformation proximate to the filter and remote from the end of the needle whereby the needle may be broken to expose a fresh point after fluid is aspirated through the needle to the syringe is filtered.

10 Claims, 2 Drawing Sheets

# FILTER NEEDLE

RELATED APPLICATION

This application is based upon Provisional Application No. 60/853,444 filed Oct. 23, 2006.

FIELD OF THE INVENTION

The present invention relates to an injection device, more particularly to a single-in line filtering needle for filtering debris while withdrawing fluid from a glass ampoule and the like and a method thereof for administering filtered drug in a single step.

BACKGROUND ART

A filter needle is a device for filtering debris from a hypodermic needle. In a typical application, a nurse, or other health care provider, will use such a device in connection with the infusion of concentrated drugs into an IV bag. The drug is stored in a glass ampoule which is opened by snapping the frangible neck. The drug can become dangerously contaminated by glass particles resulting from breaking the ampoule. Accordingly, it is necessary to filter the drug before using it. Thereafter, the filtered drug is aspirated through a fresh needle into a syringe for infusion into the IV bag.

Most filtering devices known in the art are two step devices, that is, they have at least two separate parts: one to filter the drug and the other to administer the drug.

Known devices are complicated and have separate needle parts, one with a filter and one which has no filter. In use the needle with the filter is used to aspirate a liquid into a syringe and to thereby filter debris from the aspirated liquid. The first needle is then removed and discarded and the second needle is installed and is then used to dispense liquid from the syringe. The arrangement with two parts is cumbersome to use and may result in increased bio-hazard and waste. In addition, there is increased cost due to additional equipment requirements.

The known processes are time consuming and expensive, because they require multiple steps and two needles to complete the drug administration process. The multiple needles used in the process add to bio-hazard waste disposal volume, and the extra needle handling is a source of needle stick injuries which are hazardous. Also there is a chance that the health care provider may forget to change the needle, and the filter product thus remains contaminated.

Therefore there exists a need to have an injection device that is not cumbersome and that can be used in a single step without the need for an external attachment.

There is also a need for improved safety for health care providers, and there is a need to reduce cost and bio-hazard risk and increased biological waste volume

SUMMARY OF THE INVENTION

To meet the stated objects of the invention and to overcome the disadvantages known arrangements, a disposable injection device has been provided.

The device has a cylindrical needle formed with a shaft having and inlet end, an outlet end and a hollow through passageway extending between the inlet and the outlet along a central axis of the needle for communicating fluids therethrough. The inlet end is adapted to be mounted to the outlet of a syringe. A distal end is formed with a sharp first piercing point. A filter is positioned in the passageway proximate to the first piercing point. The needle is used to aspirate liquids from a potentially debris contaminated source liquid. Such contamination is filtered by the filter as the liquid is aspirated into the syringe. A frangible deformation is formed on the shaft upstream of and proximate to the filter. When the shaft is deformed lateral forces applied on opposite sides of the deformation, stress is concentrated thereat causing the shaft to fail along the deformation, whereby the distal portion of the shaft with the filter is separated from the remainder of the shaft. In addition, a second piercing point is formed at a newly formed end of the shaft. Upon separation of the distal end portion containing the filter from the remainder of the shaft, the newly formed end is used to dispense liquid uncontaminated with debris from the syringe.

A method for using a disposable injection device employs a filter needle having a deformation upstream of the filter and sharp end. According to the method, liquid which may contain debris is aspirated into the syringe. When sufficient liquid is aspirated, the needle is stressed by lateral forces causing the needle to fail along the deformation thereby resulting in a fresh piercing point separated from a portion of the shaft containing the needle. Thereafter, the portion of the shaft containing the sharp end an the filter is discarded and the fresh point is used to dispense filtered liquid from the syringe.

BRIEF DESCRIPTION OF THE DRAWINGS

The invention and its various embodiments is better understood by reading the description along with the accompanying drawings wherein.

DESCRIPTION OF THE INVENTION

Figure 1:
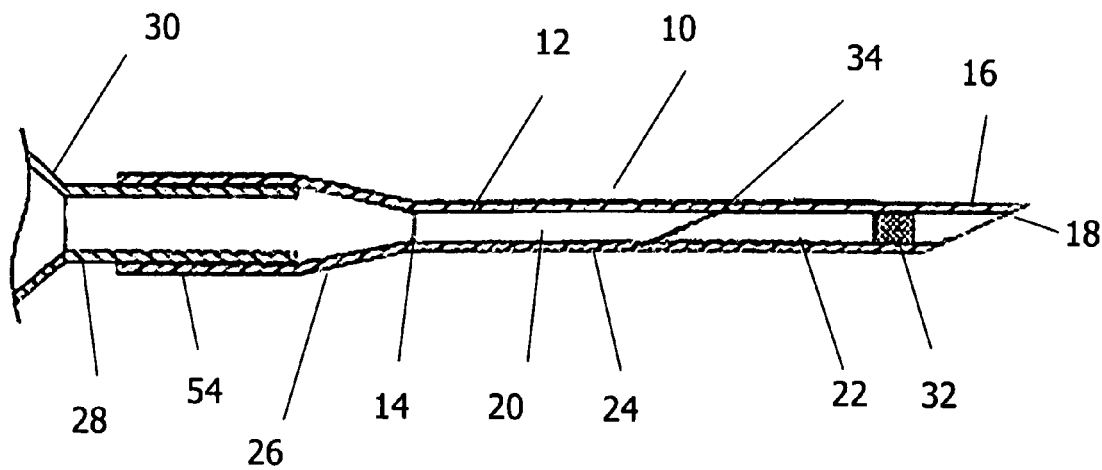
FIG. 1 shows a cross sectional view of an exemplary embodiment of the filter needle of the present invention.

Referring to FIG. 1, an exemplary embodiment of the invention is illustrated. The invention comprises a single in-line filter needle 10, formed of a hollow shaft 12, having a proximal or inlet end 14 and a distal or outlet end 16 having a first sharp point 18. The shaft is formed with a central through opening 20 having an inner wall 22 and an outer wall 24. The through opening extends between the inlet and outlet for communicating fluids there through. The fluids are typically drugs supplied in glass ampoules, which drugs may be contaminated with debris which may result from opening the ampoules in a known manner, i.e. by fracturing the ampoule along the neck portion, discussed below. The proximal end 14 of the shaft 12 secured to a leur lock 26 adapted to be snugly secured on the end or barrel 28 of conventional syringe 30 used to aspirate liquid and to dispense liquid. The needle 10 is adapted for removable connection to the syringe, whereby a liquid may be aspirated for later use. The distal end 14 may be employed without a sharp end if desired, particularly if it is not necessary to pierce an object. However, as a practical matter it is convenient to have a sharp end. It should be understood that the terms inlet and outlet are illustrative only. It will become evident that, depending on the direction of flow an end of the needle may be an inlet or an outlet. However, for purposes of the discussion normal flow of liquid is from the syringe to the inlet 12 to the outlet 14. When flow is reversed, the convention identifying the respective ends will remain the same, but may be referred to as proximal or distal for clarity.

The needle 10 shown in FIG. 1 has a filter 32 located in the through opening 20 proximate to the sharp point 18. The filter 32 is adapted to filter small particles of which may be entrained in liquids. The filter may be a fiber or non-fiber material with pores of around 0.01 microns sufficient to filter small particles which may be found in the liquid to be aspirated.

The filter 32 may include a cylindrical filter element sized and shaped to engage and seal against the inner wall of the needle. The filter may be secured by an interference fit interior of the needle. In accordance with the invention, the filter has sufficient flow capacity to allow for rapid aspiration of liquid therethrough. The density of the filter is sufficient to trap contaminants such as glass shards.

In the invention, a frangible deformation 34 may formed on the outer wall 24 of the shaft 12 between the inlet and the outlet. The deformation may be an uninterrupted or continuous score line or it may be in the form of a saw-tooth groove as shown. The frangible deformation 34 may be formed using a cutting implement to form a score line disposed at an angle to the axis of the needle, so that when the needle is stressed the new sharp point is formed. As noted above, the score line may be continuous forming a smooth fresh sharp end, or the score line may be in the form a saw-tooth in order to cause the needle to break in such a way that the fresh tip is serrated. When pressure is applied on opposite sides of the deformation 34, the shaft 12 breaks along the score line 36, thereby forming a fresh point, discussed hereinafter.

Figure 1A:
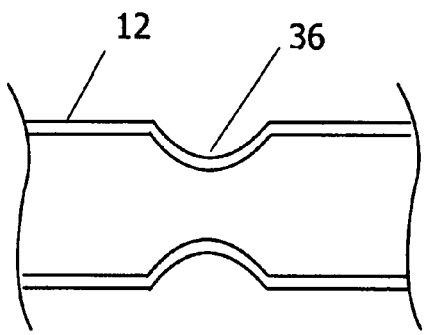
FIG. 1A is an illustration of an alternate form of a deformation formed in the needle illustrated in FIG. 1.

Other forms of deformation may be applied to the shaft as desired. For example, a radial deformation 36 may be made in the outer wall 24 of the shaft as shown in FIG. 1A. The deformation may be formed by applying pressure against the outside surface of the shaft to deform the needle shaft. A mandrel may be located inside the needle passageway during the formation of the deformation or groove so as to prevent collapse of the needle and closure of the opening.

Figure 2:
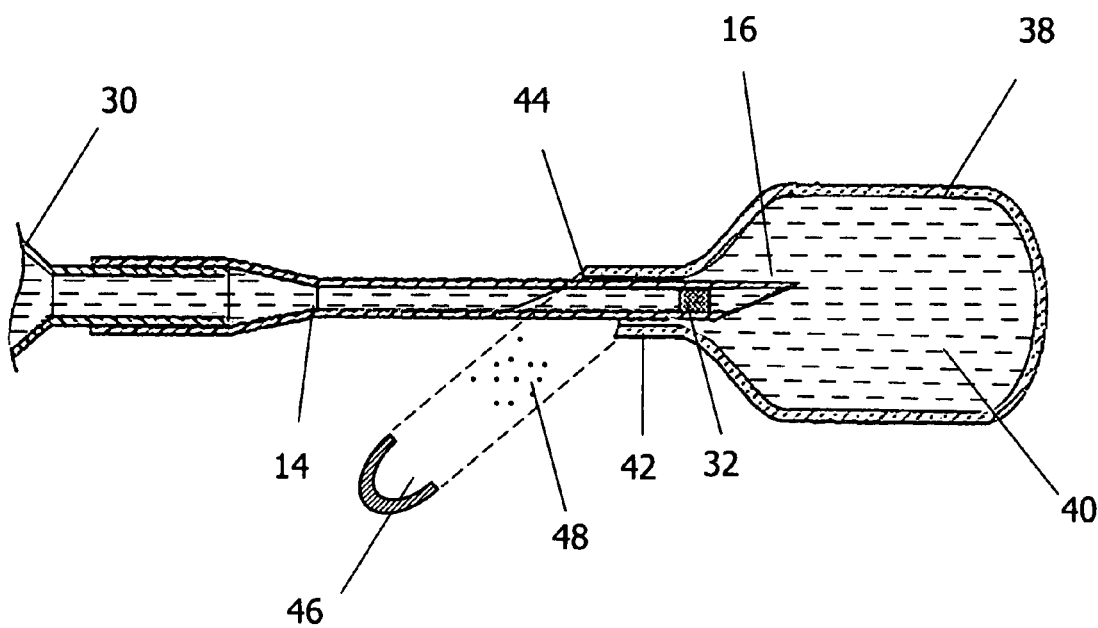
FIG. 2 shows the arrangement of FIG. 1 employed for aspirating liquid contaminated by debris from a freshly opened ampoule.

FIG. 2 shows an ampoule 38 for containing a liquid 40 therein. The ampoule has a narrow neck 42 with an irregular open end 44 formed when a closed end 46 is snapped or severed from the neck 42 in a conventional manner, i.e. by stressing the neck with a shearing force. When the ampoule is opened, debris in the form of small glass shards or particles 48 may be produced. The shards can find their way into the liquid. These particles must be removed from the liquid before it may be administered to a patient. Accordingly, the filter 32 is employed for this purpose.

The needle 10 is inserted into the neck 42 of the open ampoule 38 and the tip 16 of the needle is located therein as shown. The conventional syringe 30 is then operated to draw or aspirate the liquid 40 through the needle and into the syringe. The liquid is drawn into the needle 10 through the distal or outlet end 16, through the filter 32 in the hollow shaft 12 to the proximal end 14 and into the syringe. The liquid thus passes through and is filtered by the filter 32 as it is aspirated or drawn through the needle. The debris 48 or shards of glass are thus removed from the liquid as it is delivered to the syringe.

In accordance with the invention, filter needle 10 is changed in use. Initially the intact filter needle 10 shown in FIGS. 1 and 2 is used to aspirate liquid through the filter and into the syringe. Thereafter, the filter needle is broken along the deformation 34, leaving a remaining portion with a fresh sharp end and a severed portion which is discarded as discussed hereinafter. The deformation allows the needle to break and form the fresh sharp end, which is used to administer the aspirated liquid or drug to a patient or into an IV line.

Figure 3:
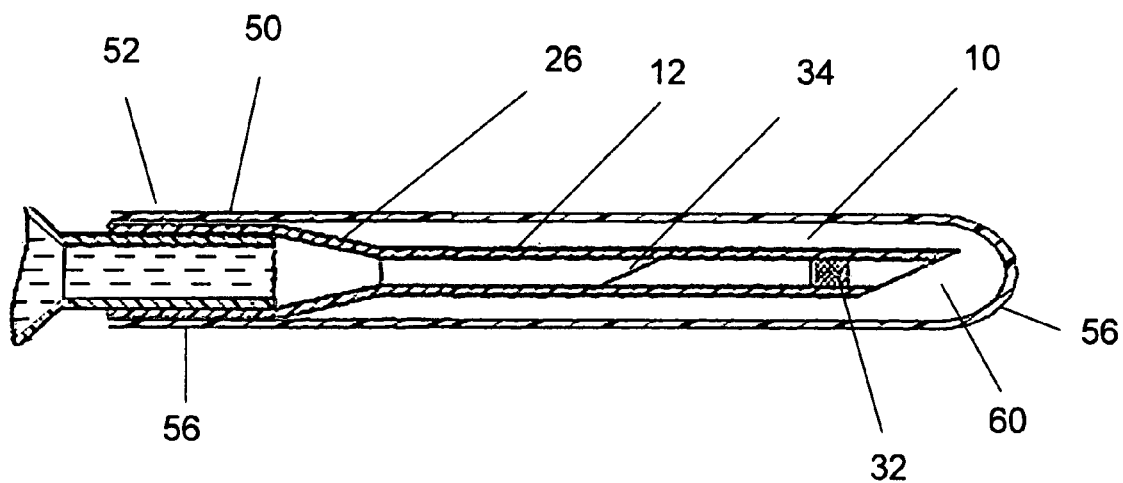
FIG. 3 is an enlarged detail showing a cover for the needle shown in FIG. 1 secured to syringe outlet.
Figure 4:
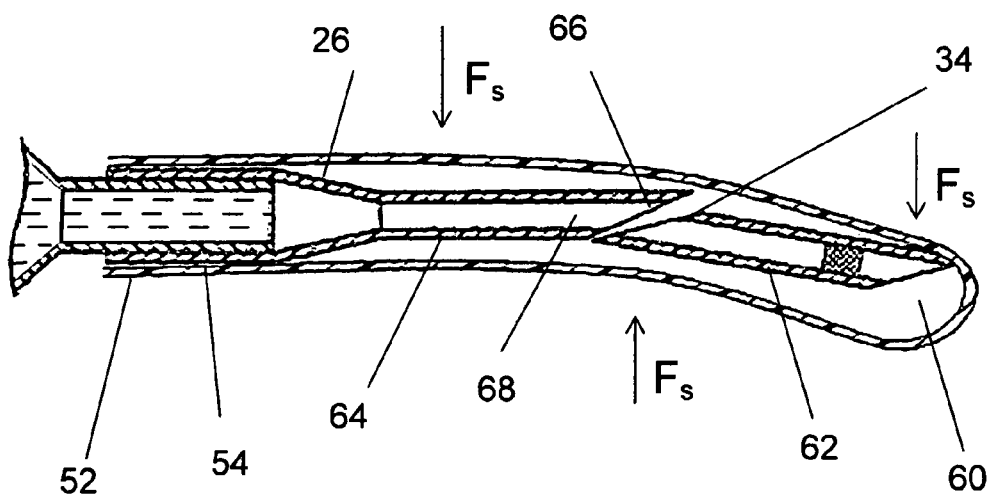
FIG. 4 illustrates the application of force to the cover to thereby stress the needle along the deformation causing the needle to break thereat to separate the portion of the needle containing the filter from the remainder of the needle and to form a fresh point along the break.
Figure 5:
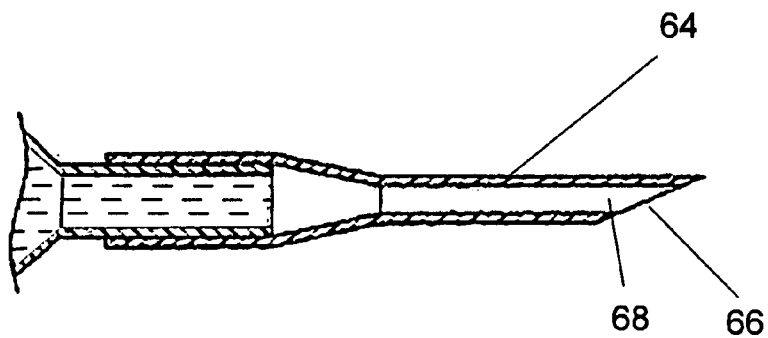
FIG. 5 illustrates the remaining portion of the needle with the fresh new point ready to infuse uncontaminated liquid.

In this connection attention is directed to FIGS. 3-5. The needle 10, having been used to filter the liquid as it is aspirated into the syringe, is enclosed by a flexible, resilient cover 50 which has an open end 52 which is snugly fit over the outer surface 54 of luer lock 26. The cover 50 has a closed end 56 and a hollow interior chamber 60. The cover has a length sufficient to enclose the needle 10 therein as shown. The cover may be a suitable polymeric material which is flexible, resilient and sufficiently thick to protect the user from a dangerous stick.

As shown in FIG. 4, after the needle is covered as shown in FIG. 3, a shearing force Fs is applied to the cover 50 on either side of the deformation 34. Typically, the user may place thumbs on the cover in opposition to the deformation and place the index finger of each hand on the cover adjacent the deformation. The frangible deformation around the circumference of the needle is thus configured to fracture with a predefined pressure.

The opposing shear forces of the thumbs applied to the cover behind the deformation, and the force of the index fingers placed on the cover adjacent each side of the deformation creates the cover to bend and to transfer to the shaft a shear stress along the deformation causing the shaft to fail or break in such a way that there is formed a broken off tip portion 62 trapped in the closed cover and a remaining portion 64 having a fresh sharp end 66 formed along the break and a new outlet 68.

The cover 50 acts to transfer shear forces to the needle shaft and to protect the user during the step of applying stress forces on the deformation. After the needle is broken, the cover with the broken off tip 60 located there in are removed from the syringe barrel, and they may be immediately discarded or discarded later. In this way, contaminants, such as glass shards trapped in the filter may be removed from the field. The remaining portion 64 of the needle 10 with the fresh point 66 is then available for use in dispensing uncontaminated drug from the syringe by piercing an IV bag or line.

The drug is dispensed from the syringe through the inlet 64 the channel and through the fresh sharp end 66 and newly formed outlet 68. When the drug is dispensed, the syringe and remaining portion 64 of the needle may be discarded along with the cover and broken end of the needle. The cover, because it is resilient generally recovers its original shape and it and the broken off portion of the needle trapped therein, may be reinstalled over the needle and the entire assembly may be discarded in a safe manner as a unit.

What is claimed is:

1. A method for using a disposable injection device, wherein a cylindrical needle has an integral shaft with an outer surface, a proximal end with an inlet, a distal end with an outlet and a passageway along a longitudinal axis to a dispensing device, the passageway for communicating fluids therethrough between the inlet and the outlet, the proximal end adapted to be mounted to the outlet of the dispensing device, the distal end with a first piercing point;

a frangible deformation in the outer surface of the needle;

a filter in the passageway downstream of the frangible deformation and near the distal end, comprising the steps of:

aspirating a liquid through the outlet at the distal end into said passageway through the said filter and through the inlet end at the proximal end to the dispensing device;

filtering the liquid as it passes through the filter;

breaking the needle along the said frangible deformation to thereby separate the distal end of the needle with the filter and to form a fresh piercing point along the deformation; and wherein the breaking step further comprises installing a resilient cover over the needle enclosing the frangible deformation therewithin, applying the shear forces to the cover, transferring the shear forces to the needle through the cover and removing the cover and separated part after the breaking step.

2. The device of claim 1 wherein the frangible deformation is a serrated line.

3. The device of claim 1 wherein the frangible deformation is a groove formed in the outer wall of the needle.

4. The device of claim 1 wherein the said filter comprises a fibrous filtering medium.

5. The device of claim 1 wherein the said filtering means is a non-fibrous filtering medium.

6. The device of claim 1 wherein the filter medium has a size sufficient to filter debris from the medium.

7. The device of claim 1 wherein filter has a size sufficient to trap debris of about 0.1 micron in size.

8. The method of claim 1 further comprising reinstalling the resilient cover and separated part therein over the needle and discarding the assembly.

9. A disposable injection device comprising:

a cylindrical needle having an integral shaft with a central axis and an outer surface, a proximal end with an inlet end, a distal end with an outlet and a first sharp point thereat, and a central through opening forming a passageway through the shaft aligned with the central axis extending between the inlet and the outlet for communicating a liquid therethrough;

a luer attached to the proximal end of the shaft for connection to a syringe;

a filter positioned in the passageway proximate to the said first piercing point for filtering relatively small contaminating particles from the liquid;

a frangible deformation formed in the outer surface of the said shaft proximate to and upstream of the filter;

an elongated resilient flexible cover having an open end, a closed end, and an interior chamber, the cover being disposed over the needle about the frangible deformation, the open end being snugly fit over the luer for securing the cover thereto; and said cover for covering the needle as a force is applied thereto, and for transferring the force to the needle therein for imparting sufficient stress to the frangible deformation causing the shaft to break therealong and to form a fresh point thereat, and to thereby separate a distal portion of the needle containing the filter and first sharp point form from a remaining portion of the needle, the cover being removable to expose the fresh point.

10. The disposable injection device of claim 9 wherein the needle and leur comprises a one piece construction.

* * * * *